United States Patent [19]

Rajoharison

[11] Patent Number: 5,124,459

[45] Date of Patent: Jun. 23, 1992

[54] PROCESS FOR THE PREPARATION OF 3-(3-PYRIDYL)-1H,3H-PYRROLO[1,2-C]THIAZOLE-7-CARBONITRILE

[75] Inventor: Harivelo G. Rajoharison, Echirolles, France

[73] Assignee: Rhone-Poulenc Sante, Antony, France

[21] Appl. No.: 298,943

[22] Filed: Jan. 19, 1989

[30] Foreign Application Priority Data

Jan. 20, 1988 [FR] France .................................. 88 00591

[51] Int. Cl.$^5$ .......................................... C07D 401/00
[52] U.S. Cl. .................................................... 546/270
[58] Field of Search ............................... 546/280, 270

[56] References Cited

U.S. PATENT DOCUMENTS 4,657,908  4/1987  Yellin et al. ........................ 546/141

FOREIGN PATENT DOCUMENTS 0115979  8/1984  European Pat. Off. ............ 546/270

Primary Examiner—Patricia L. Morris
Assistant Examiner—Robert C. Whitenbaugh
Attorney, Agent, or Firm—Morgan & Finnegan

[57] ABSTRACT

3-(3-Pyridyl)-1H,3H-pyrrolo[1,2-c]thiazole-7-carbonitrile is prepared by the action of 2-chloroacrylonitrile on a salt of 3-formyl-2-(3-pyridyl)-4-thiazolidinecarboxylic acid with an organic base in the presence of an acid chloride in an organic solvent capable of dissolving the salt.

6 Claims, No Drawings

PROCESS FOR THE PREPARATION OF 3-(3-PYRIDYL)-1H,3H-PYRROLO[1,2-C]THIAZOLE-7-CARBONITRILE

The present invention relates to the preparation of 3-(3-pyridyl)-1H,3H-pyrrolo[1,2-c]thiazole-7-carbonitrile of formula:

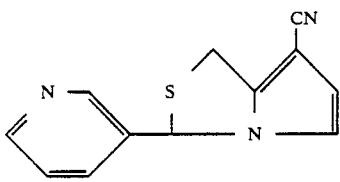

which is useful as an intermediate in the preparation of medicines intended for the treatment of conditions in which the physiological role of PAF-acether is involved, particularly for the treatment of allergies and inflammation and for preventing blood platelet aggregation. Such products are known from European Patent Specification No. 0,115,979.

Up to the present, 3-(3-pyridyl)-1H,3H-pyrrolo[1,2-c]thiazole-7-carbonitrile has been prepared by the process described in European Patent No. 0 115 979 from 3-formyl-2-(3-pyridyl)-4-thiazolidinecarboxylic acid according to the following reaction:

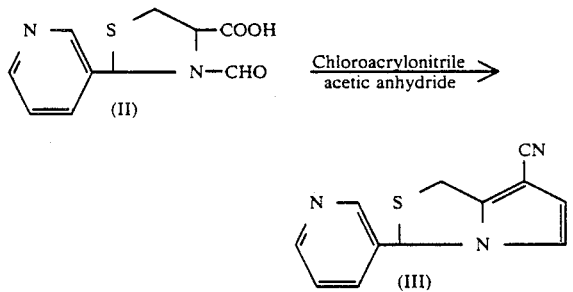

This synthesis has two principal disadvantages:
Whatever the purity of the formylated acid of formula (II) that is used, large quantities of tar are always obtained, necessitating awkward purification operations and resulting in low yields (of the order of 15%).
The condensation of chloroacrylonitrile with the acid of formula (II) requires 5 equivalents of chloroacrylonitrile per mole of acid, which necessitates recovering and recycling the chloroacrylonitrile if the process is to be operated on an industrial scale.

It has now been found, and this constitutes the subject of the present invention, that these disadvantages can be avoided by replacing acetic anhydride by an acid chloride, using a solvent which dissolves the acid of formula (II) in the form of a salt with an organic base.

In practice, the reaction is generally carried out in a chlorinated organic solvent which can dissolve the salt of the acid of formula (II), such as dichloromethane or dichloroethane, operating at a temperature between −65° C. and the reflux temperature of the reaction mixture in the presence of the selected acid chloride.

A trialkylamine such as triethylamine, tributylamine or pyridine may be used as an organic base to form the salt of the acid of formula (II).

It is particularly advantageous to use para-toluenesulphonyl chloride, methanesulphonyl chloride, oxalyl chloride or phosphorus oxychloride as the acid chloride.

The nitrile of formula (I) may be purified by the customary means known to those skilled in the art, e.g. by chromatography or recrystallization.

The acid of formula (II) may be prepared according to the method described in European Patent 0 115 979.

The following Examples show in a more detailed manner how the invention may be carried out in practice.

EXAMPLE 1

Triethylamine (7.67 g) is added to a suspension of 3-formyl-2-(3-pyridyl)-4-thiazolidinecarboxylic acid (4.47 g) in dichloromethane (40 cc) at a temperature close to 20° C. A clear, light yellow solution is obtained. The mixture is cooled to −65° C. and then phosphorus oxychloride (1.84 g) is added dropwise in the course of 10 minutes. The initial suspension gives way to a purple-red homogeneous mixture. This is stirred for 1 hour at −65° C. and then 2-chloroacrylonitrile (4.38 g) is added quickly in the course of 4 minutes. The reaction mixture is allowed to return gradually in the course of 1 hour to a temperature close to 20° C. Dichloromethane (20 cc) is then added and the mixture is heated to 40° C. for 1 hour. After cooling to room temperature, water (20 cc) and an aqueous solution of sodium hydroxide (10 cc, 0.5N) are added. The organic phase is decanted and the aqueous phase extracted several times with dichloroethane. The organic extracts are combined and dried overnight over sodium sulphate. After filtration, the solvent is evaporated off under reduced pressure (20 mm Hg; 2.7 kPa) at 40° C.; a crude product (2.95 g) is obtained. This product is chromatographed on a column (diameter 25 mm) containing silica 50 g) (0.063-0.2 mm), eluting with ethyl acetate. 7-Cyano-3-(3-pyridyl)-1H,3H-pyrrolo[1,2-c]thiazole (1.84 g) is thereby obtained in the form of cream-coloured crystals, m.p. 110° C. (yield 40% relative to the acid used).

EXAMPLE 2

Triethylamine (3.1 cc) is added dropwise in the course of 15 minutes to a stirred suspension of 3-formyl-2-(3-pyridyl)-4-thiazolidinecarboxylic acid (4.77 g) in 1,2-dichloroethane (30 cc) in the presence of a few hydroquinone crystals, at a temperature close to 20° C. A homogeneous light yellow mixture is obtained. Then a solution of oxalyl chloride (2.76 g) in 1,2-dichloroethane (10 cc) is added in the course of 1 hour and 10 minutes at a temperature close to 20° C. The reaction mixture becomes heterogeneous and ochre in colour. A solution containing 2-chloroacrylonitrile (2 g), triethylamine (6.15 cc) and 1,2-dichloroethane (10 cc) is then added in the course of 20 minutes at 20° C. The mixture is stirred for 1 hour at a temperature close to 20° C., and then heated to 40° C. for 1 hour. After cooling, distilled water (75 cc) is added. The organic phase is decanted, dried over sodium sulphate and then assayed by HPLC. It contains 7-cyano-3-(3-pyridyl)-1H,3H-pyrrolo[1,2-c]thiazole (2.51 g), i.e. a yield of 55% relative to the acid used.

EXAMPLE 3

3-Formyl-2-(3-pyridyl)-4-thiazolidinecarboxylic acid (10 g) is suspended in dichloromethane (15 cc) in a 50 cc three-necked flask equipped with a condenser, a dropping funnel, a magnetic stirrer, a thermometer and a gas-holder. Then triethylamine (4.8 g) is added at 20° C. A homogeneous colourless solution is obtained. This solution is added dropwise in the course of 50 minutes and at 25° C. to a stirred mixture of methanesulphonyl chloride (5.29 g) and dichloromethane (17 cc). 2-Chloroacrylonitrile (4.04 g) is then added quickly, followed at 20°–35° C. and over the course of one hour, by triethylamine (9.35 g) and dichloromethane (5 cc). The mixture is then refluxed for 50 minutes. After cooling, it is hydrolysed with water (12 cc). The organic phase is decanted and the aqueous phase extracted with dichloromethane. The organic extracts are combined and dried overnight over sodium sulphate. After filtering, the solvent is evaporated off under reduced pressure 20 mm Hg; 2.7 kPa) at 20° C. A crude product (9 g) is obtained, and is purified by chromatography on a column diameter 4.5 cm) containing silica (100 g) (0.063–0.2 mm), eluting with a mixture of ethyl acetate and dichloromethane. 7-Cyano-3-(3-pyridyl)-1H,3H-pyrrolo[1,2-c]thiazole (7.10 g) is thereby obtained in the form of light beige-coloured crystals m.p. 108° C. (yield 82.5% relative to the acid used).

EXAMPLE 4

Triethylamine (4.67 g) is added to a suspension of 3-formyl-2-(3-pyridyl)-4-thiazolidinecarboxylic acid (10 g) in dichloromethane (15 cc) at a temperature close to 20° C. A clear light yellow solution is obtained. This solution is added dropwise in the course of 1 hour at 40° C. to a mixture of tosyl chloride (8.8 g) in dichloromethane (17 cc). The reaction mixture becomes homogeneous and orange-red in colour. 2-Chloroacrylonitrile (4.10 g) is then added quickly, followed, while the reaction medium is maintained at reflux, by triethylamine (9.37 g). The reaction mixture is maintained refluxing for a further 1 hour and 25 minutes. After cooling to room temperature, the reaction medium is hydrolysed with water (12 cc). The organic phase is decanted and the aqueous phase extracted with dichloromethane. The organic extracts are combined and dried overnight over sodium sulphate. After filtering, the solvent is evaporated under reduced pressure (20 mm Hg; 2.7 Pa) at 20° C. A crude product (11.11 g) is obtained, and is purified by chromatography on a column (diameter 4.5 cm) containing silica (100 g) (0.063–0.2 mm), eluting with a mixture of ethyl acetate and dichloromethane. 7-Cyano-3-(3-pyridyl)-1H,3H-pyrrolo[1,2-c]thiazole (8.36g) is thereby obtained in the form of light beige-coloured crystals, m.p. 110° C. (yield 88.4% relative to the acid used).

I claim:

1. A process for the preparation of 3-(3-pyridyl)-1H-pyrrolo[,1,2-c]thiazole-7-carbonitrile of formula:

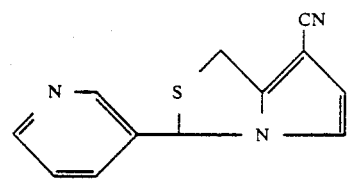

which comprises reacting 3-formyl-2-(3-pyridyl)-4-thiazolidinecarboxylic acid of formula:

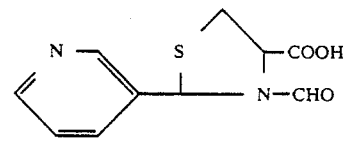

in the form of a salt with an organic base, with 2-chloroaorylonitrile in the presence of an acid chloride and of an organic solvent capable of dissolving the said salt.

2. Process according to claim 1, wherein the acid chloride used is para-toluenesulphonyl chloride, methanesulphonyl chloride, oxalyl chloride or phosphorus oxychloride.

3. Process according to claim 1, wherein the base used to form the salt with the acid of formula (II) is a trialkylamine or pyridine.

4. Process according to claim 3, wherein the said base is triethylamine.

5. Process according to claim 1 wherein the organic solvent used is a chlorinated solvent.

6. Process according to claim 5, wherein the said solvent is dichloromethane or 1,2-dichloroethane.

* * * * *